United States Patent [19]

Neuman et al.

[11] Patent Number: 4,646,719
[45] Date of Patent: Mar. 3, 1987

[54] INTRA-AORTIC BALLOON CATHETER HAVING FLEXIBLE TORQUE TRANSMITTING TUBE

[75] Inventors: Harold L. Neuman, Reading; Edward J. Lombardi, Malden, both of Mass.

[73] Assignee: Aries Medical Incorporated, Woburn, Mass.

[21] Appl. No.: 619,015

[22] Filed: Jun. 11, 1984

[51] Int. Cl.⁴ .............................................. A61B 19/00
[52] U.S. Cl. .................................... 128/1 D; 128/344
[58] Field of Search ............ 128/1 D, 325, 344, 348.1; 604/96–103

[56] References Cited

U.S. PATENT DOCUMENTS

| | | | |
|---|---|---|---|
| 3,585,983 | 6/1971 | Kantrowitz et al. | 128/344 X |
| 4,276,874 | 7/1981 | Wolvek et al. | 128/1 D |
| 4,362,150 | 12/1982 | Lombardi et al. | 128/1 D |
| 4,402,307 | 9/1983 | Hanson et al. | 128/1 D |
| 4,444,186 | 4/1984 | Wolvek et al. | 128/1 D X |

*Primary Examiner*—Dalton L. Truluck
*Attorney, Agent, or Firm*—David G. Conlin; George W. Neuner; Ronald I. Eisenstein

[57] ABSTRACT

A balloon catheter is disclosed which is flexible yet transmits positive torque when rotated in the direction for unwrapping the balloon. The balloon catheter comprises a hollow catheter having a proximate end and a distal end, an inflatable and deflatable balloon having a proximate end and a distal end, said proximate end of the balloon being sealably attached to the distal end of the catheter for admitting fluid (generally a gas) and withdrawing fluid from the balloon, and a flexible central lumen disposed within said hollow catheter and having a proximate end and a distal end, said distal end of said central lumen being sealably attached to the distal end of the balloon, said central lumen comprising a flexible core wrapped spirally with a spring-like material so that the wrapped core can transmit positive torque when rotated in one direction. Preferably, the flexible core is made of a polymeric or elastomeric tube so that access to the aorta can be obtained through it.

13 Claims, 9 Drawing Figures

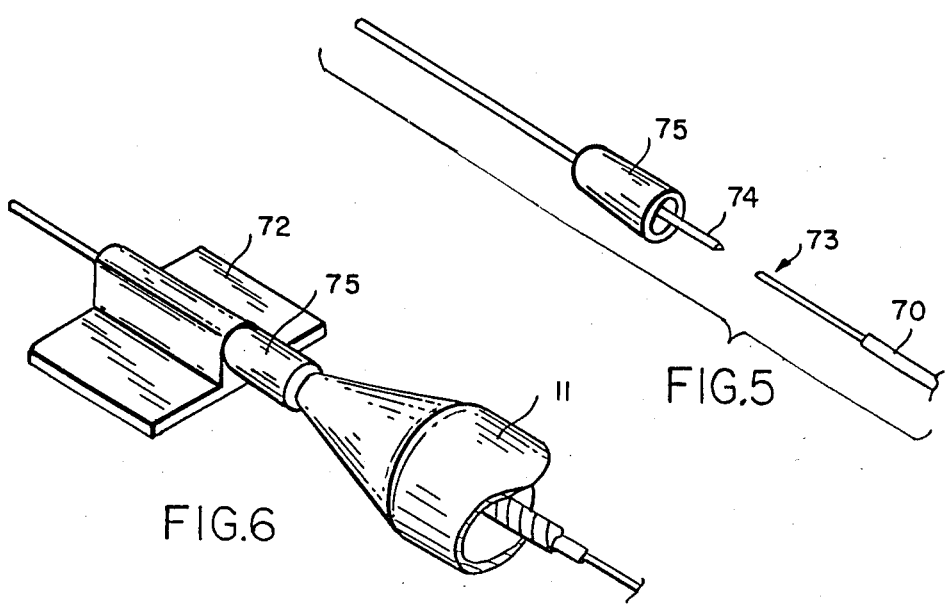
FIG.5
FIG.6
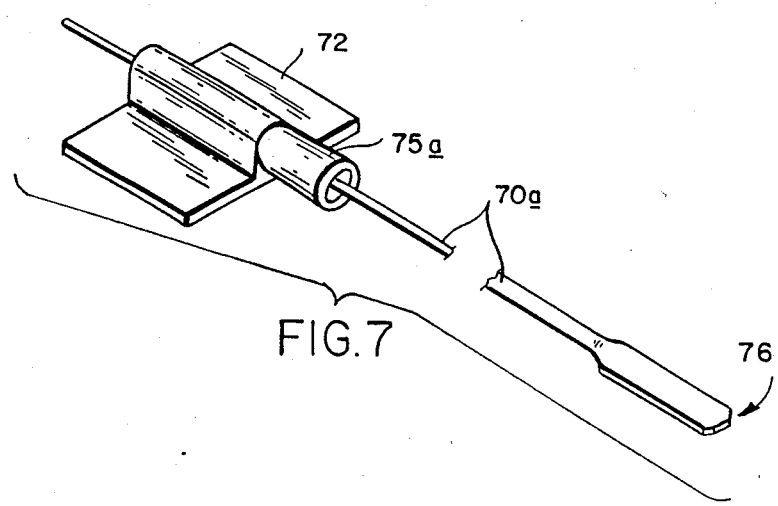
FIG.7
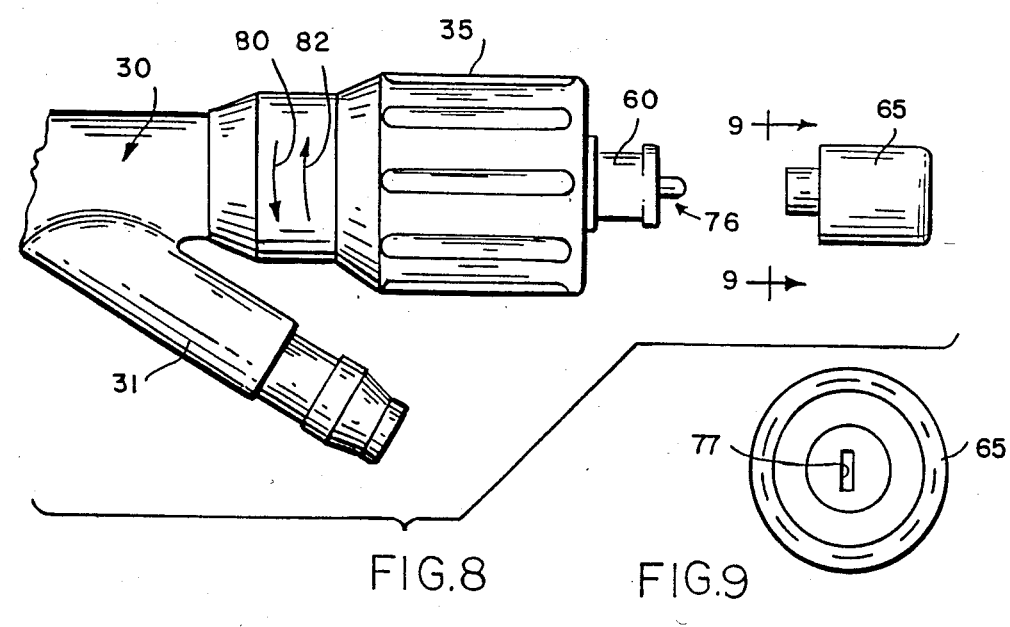
FIG.8
FIG.9

INTRA-AORTIC BALLOON CATHETER HAVING FLEXIBLE TORQUE TRANSMITTING TUBE

FIELD OF THE INVENTION

This invention relates to intra-aortic balloon pumps and particular to improved balloon catheters having a longitudinally flexible, torque transmitting tube.

BACKGROUND OF THE INVENTION

Intra-aortic balloon pumping is a recognized method of cardiac assistance for a failing heart. The original indications for intra-aortic balloon pumping in cardiogenic shock due to acute infarction, post-operative severe low cardiac output state, or inability to wean from cardiopulmonary bypass have been extended to include treatment for refractory unstable angina in the period before and after infarction, recurrent life-threatening tachyarrhythmias, preoperative support in the presence of severe left ventricular dysfunction and reduction of infarct size.

During the first few years following the introduction of the intra-aortic balloon pump for clinical use in 1968, balloon catheters were the subject of considerable development and design efforts. In the 1970's, most of the efforts in the field of intra-aortic balloon pumping were directed mainly toward clarifying the indications for and to reporting large clinical experiences with this therapeutic modality. During this period, no major advances in balloon catheter technology were made.

Catheter for intra-aortic balloon pumping typically have utilized a nonstressed or nondistendable balloon, i.e., the balloon is not stretched during inflation and deflation and doesn't substantially change its surface area, inflating and deflating with a predetermined volume of appropriate fluid to achieve phasic operation; the balloon surface area is always substantially equal to that of a fully inflated balloon.

It has been recognized in the prior art that insertion and guiding of catheters in patients is difficult and that trauma and damage to the incision and blood vessel may occur during said insertion and guiding. In some prior art catheters, in order to permit insertion and guiding of the catheter in a blood vessel, the balloon is rolled or spirally wrapped around its underlying central lumen. See for example, FIGS. 3 and 4 of Goetz et al., U.S. Pat. No. 3,692,018. This makes the catheter more compact. In Grayzel, U.S. Pat. No. 3,939,820, the size of the catheter can be reduced by replacing the catheter tube within the balloon by a wire. However, the balloon is nonetheless spirally wrapped around the wire. Additionally, the wire in Grayzel is relatively inflexible to support the balloon.

Insertion of the balloon catheter is conventionally performed in accord with the standard Seldinger technique which is a non-surgical insertion through the skin (percutaneously) developed in the late 1950's. One type of known percutaneous intra-aortic balloon catheter comprises a single chamber balloon sealably disposed at the end of a catheter. The extreme end of the balloon is internally bonded to a stiff wire disposed within the balloon and which terminates at a swivel located at the junction of the catheter and the balloon. The balloon is wrapped around the wire by grasping the catheter and twisting the remote end of the balloon until the desired degree of wrapping is obtained. After the balloon is wrapped the application of a vacuum to the interior of the balloon is relied on to maintain the balloon in its wrapped condition. Neither during nor after insertion is access to the interior of the aorta available. Application of pressure to the interior of the balloon, together with manual rotation of the catheter, is relied on to effect unwrapping of the balloon and permit pumping to begin.

Other balloon catheters having additional mechanical features such as flexible tips, elongating tips, rotating members, etc. have been described in, for instance, U.S. Pat. Nos. 4,261,339; 4,276,874; 4,327,709; 4,346,698; 4,362,150 and 4,402,307.

However these prior art balloon catheters are typically made with stiff surgical steel tubes, with or without flexible tips to lessen or prevent trauma to the blood vessel during insertion, or from flexible polymeric tubing which has no positive torque transmission capability. The first type balloon catheters are uncomfortable in the patient and care must be taken by the patient to avoid trauma. A guide wire is required for insertion. The second type is relatively comfortable after insertion but lacks positive control of the unwrapping of the balloon due to the resilient nature of the polymeric tubing under rotational force and to the inability of such tubing to transmit positive torque. Thus, these type balloon catherers require a stylet to assure unwrapping. However, certain situations require a guide wire for insertion into the patient. The use of a guide wire and a stylet are mutually exclusive. Thus, a majority of the balloons having a soft central lumen do not unwrap properly when the wrapping stylet is removed. Incomplete unwrapping can cause clotting.

Thus, it can be seen that it would be highly desirable to have a balloon catheter with the flexible properties of the polymeric tubing central lumen to increase comfort while providing positive rotational torque transmission to insure complete unwrapping of the balloon after insertion.

SUMMARY OF THE INVENTION

The present invention provides such a balloon catheter which is flexible yet transmits positive torque when rotated in the direction for unwrapping the balloon. Thus, the balloon catheter of the present invention comprises a hollow catheter having a proximate end and a distal end, an inflatable and deflatable balloon having a proximate end and a distal end, said proximate end of the balloon being sealably attached to the distal end of the catheter for admitting fluid (generally a gas) and withdrawing fluid from the balloon, and a flexible central lumen disposed within said hollow catheter and having a proximate end and a distal end, said distal end of said central lumen being sealably attached to the distal end of the balloon, said central lumen comprising a flexible core wrapped spirally with a spring-like material so that the wrapped core can transmit positive torque when rotated in one direction. Preferably, the flexible core is made of a polymeric or elastomeric tube so that access to the aorta can be obtained through it.

The balloon is thus fixedly and sealably attached at one end (proximately) to the catheter and at the other end (distally) it is fixedly and sealably attached to the central lumen which is disposed within and extends the length of the catheter. The catheter is terminated in a bifurcation or wye member, one arm of which receives the central lumen and the other arm of which is adapted for connection to a conventional pumping console for effecting pumping of the balloon through the catheter in the passageway formed between the central lumen and the inside wall of the catheter. The opposite end of the central lumen remote from the balloon is fixedly and sealably attached to wrapping means carried by the bifurcation or wye member for effecting rotation of the central lumen within the catheter and thereby enabling the furling and unfurling of the balloon about the central lumen.

The balloon is furled around the central lumen prior to insertion of the balloon catheter into the patient. The balloon is furled by rotating the central lumen in the clockwise direction, i.e. in the direction in which the spiral of the spring-like material tends to open. The balloon is unfurled under positive torque provided by the spiral wrap of the spring-like material when rotated counter-clockwise, i.e. the direction in which the spiral tends to close. Thus, the central lumen having spiral wrap in accord with the present invention provides positive torque transmission to insure unfurling of the balloon while providing relative comfort to the patient.

In use, the balloon is pumped in the conventional manner via the catheter and access through the extreme end of the balloon is provided to the interior of the aorta through the central lumen, when hollow. Preferably, when the central lumen has a hollow core, a stylet or stiff wire member is provided for insertion in and along the entire length of the central lumen to prevent bending of the central lumen when the balloon is being furled around the central lumen. The hollow core also permits use of a guide wire to facilitate inserting the balloon into the aorta and positioning of the balloon at its desired location.

The present invention permits quick and easy insertion of an intra-aortic balloon pump through the skin using any suitable catherization technique such as the aforementioned Seldinger technique. The present invention also permits furling of the balloon before insertion and provides for controlled and positive unfurling of the balloon after is has been inserted due to the positive torque transmission of the central lumen having a spiral wrap in accord with this invention.

BRIEF DESCRIPTION OF THE DRAWINGS

FIG. 5 is a partial prospective view of a swivel cup and swivel tube, and the end of a stylet illustrating one embodiment for furling the balloon catheter of the present invention.

FIG. 6 is a partial prospective view of a swivel mount and the swivel cup and tube of FIG. 5 mounted on the end of a balloon catheter in accord with the present invention.

FIG. 7 is a prospective view, partially broken away, and having an enlarged view of the locking end, of a swivel mount and swivel cup having a stylet rod imbedded therein illustrating a second embodiment for furling the balloon catheter of the present invention.

FIG. 8 is a partial side elevational view, partially exploded, of the wye end of a balloon catheter in accord with the invention illustrating a stylet male luer lock for attaching to the flattened end of the stylet illustrated in FIG. 7.

FIG. 9 is a cross-sectional view along 9—9 of FIG. 8 further illustrating the stylet male luer type of fitting.

DETAILED DESCRIPTION OF THE INVENTION

Figure 1:
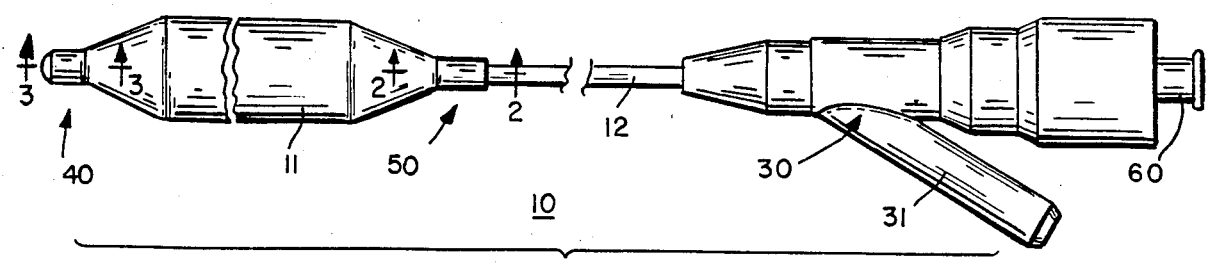
FIG. 1 is a side elevation of intra-aortic balloon catheter in accord with one embodiment of the present invention having a portion of the catheter tube and of the balloon broken away and illustrating the balloon in the unfurled (inflated) condition

As illustrated in FIG. 1, one embodiment of a balloon catheter in accord with the present invention comprises a conventional single chamber intra-aortic balloon 11 attached to a catheter 12 that terminates in a wye connector 30. The wye connector 30 provides access to inflate and deflate the balloon 11 through conduit 31.

Figures 2, 3:
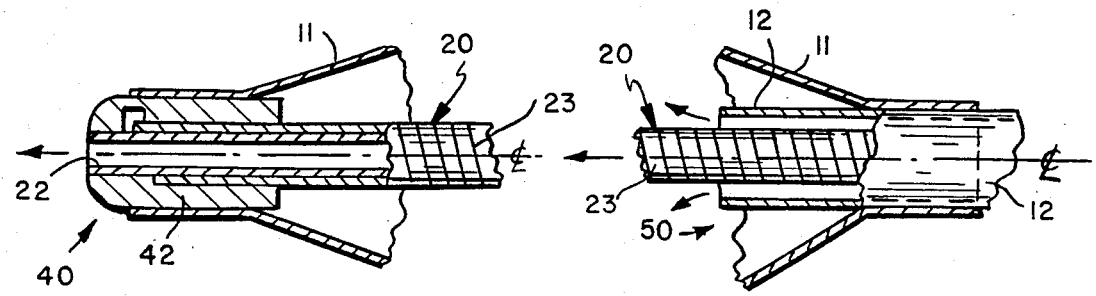
FIG. 2 is a partial cross-sectional view through section 2—2 of FIG. 1 illustrating the attachment of the proximate end of the balloon to the distal end of the catheter.
FIG. 3 is a partial cross-sectional view through section 3—3 of FIG. 1 illustrating the tip of the balloon catheter where the distal end of the balloon is attached to the flexible spirally-wrapped central lumen.
Figure 4:
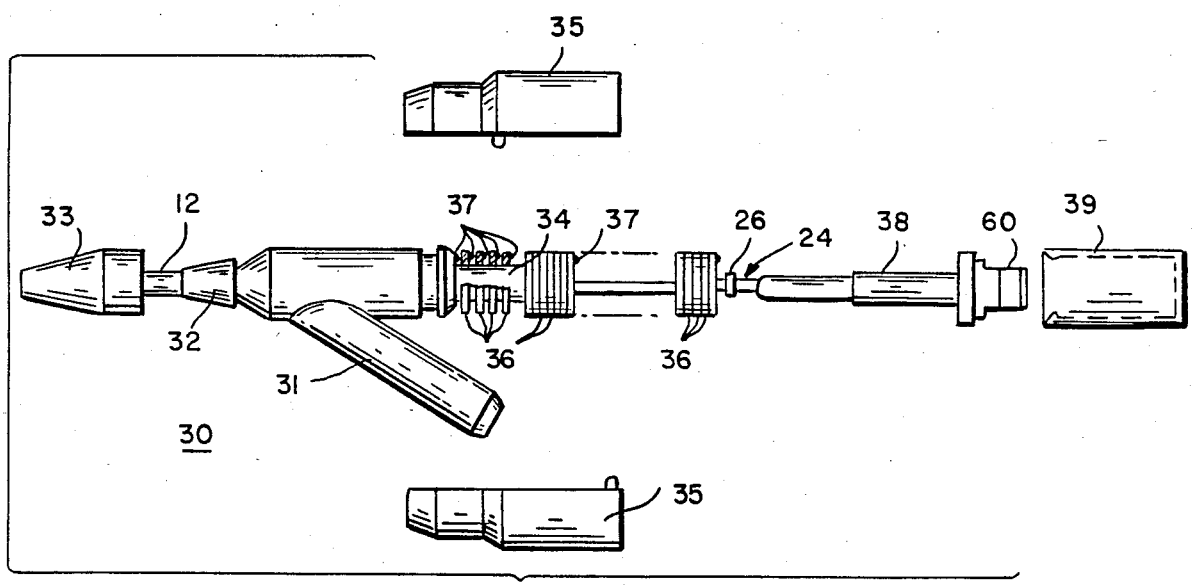
FIG. 4 is a side elevational view, partially exploded and partially in cross-section, of the proximate end of the balloon catheter apparatus illustrated in FIG. 1.

A conventional catheter 12 is sealably attached at its distal end 50 to the proximate end of the balloon 11 as illustrated in more detail in FIG. 2. A central lumen 20 extends longitudinally throughout the catheter 12 and has a distal end 40 fixedly attached to the distal end of balloon 11 as illustrated in more detail in FIG. 3. The proximate end 24 of the central lumen 20 terminates in wye 30 at luer assembly 38.

The central lumen 20 is preferably made of a flexible hollow tube 22 comprising an elastomeric or polymeric material. Around this hollow tube 22 is wrapped a spiral 24 of a spring-like material preferably a wire. Preferably, the spiral wrap is a flat wire stock to minimize resistance to fluid flow between the central lumen 20 and the interior wall of the catheter 12 when the balloon is being inflated and deflated. Any material typically used for catheters can be used to make the hollow tube 22. Preferably, the spriral wrap is made of a surgical grade stainless steel. However, other materials such as, for example, spring steel or plastic materials formed in a spiral wrap can be uséd because the spiral wrap does not come in contact with the patient because it is sealed within the catheter 12 and balloon 11.

Wye 30 provides means for inflating and deflating the balloon through conduit 31, means for furling and positively unfurling the balloon after insertion into the patient and positioning of the balloon in the aorta, and means for accessing the inside of the aorta through the hollow tube 22 of central lumen 20. The catheter 12 is sealably attached to wye 30 by slipping it over a relief seal surface having a tapered shape 32. The catheter end is attached firmly by means of fitting 33 which applies a pressure seal. The seal can be aided by application of heat or of an adhesive composition applied at 32.

The means for furling and positively unfurling the balloon in this embodiment of the invention is provided by a series of washers 36 inserted around leg 34 of the wye and held on by retainer sleeve 39. When the wye 30 is assembled, luer assemoly 38 which is sealably attached to the distal end of central lumen 20 is positioned inside leg 34 so that the ring seal 26 prevents any fluid flow or leakage out of the proximate end of the wye. Fluid, preferably helium, pumped into conduit 31 must then flow within catheter 12 along the flexible member 20 into the balloon 11. Retainer sleeve 39 compresses the washers 36 within handle 35 so that the handle can be turned one revolution for each washer. The raised portion 37 on one side of each washer 36 rotates within a corresponding annular recess on the other side of the adjacent washer. Rotation within the recess is limited to about one revolution.

The luer assembly 38 of wye 30 terminates in a standard luer type of fitting fitting 60. This fitting provides access to the inside of hollow tube 22 and thus to the aorta, if desired. A guide wire can be inserted through this fitting into the balloon catheter assembly 10 to aid in inserting and positioning the balloon catheter within the aorta. After positioning, the guide wire is removed and the highly flexible balloon catheter assembly of the present invention is relatively comfortable to the patient during operation of the balloon pump. The patient can thus move more freely with lessened risk of trauma to the blood vessel.

The balloon catheter 10 of the present invention is assembled with the balloon 11 in the fully unfurled (inflated) condition and the washers 36 and handle 35 in the furling assembly of wye 30 positioned so that there can be no rotation in the direction in which the spiral wrap 23 of the interior central lumen 20 applies positive rotational torque (i.e. tends to close the spiral). The balloon 11 is then ready to be furled prior to insertion into the patient. The balloon 11 is furled around internal central lumen 20 by rotating the washer and handle in the clockwise direction 82 as illustrated in FIG. 8 for a spiral wrap as illustrated in FIGS. 2 and 3, i.e. in the direction opposite to that which transmits positive rotational torque to the central lumen 20. When the balloon is sufficiently furled, the balloon catheter is ready to be inserted and properly positioned within the patient.

Because the interior flexible member 20 does not transmit positive rotational torque in the direction rotated during the balloon furling operation (i.e. the spiral wrap tends to unwrap), it is generally preferred to insert a stylet into the central lumen 20 to aid in furling the balloon. In one embodiment, a stylet 70 having an end 73 with a reduced cross-section of a convenient shape or spline (FIG. 5) is inserted into the central lumen from the proximate end. A swivel cup 75 having a swivel tube 74 mounted therein is inserted into the central lumen from the distal end. The reduced cross-section of the end 73 of the stylet has a shape that slips into and locks in the swivel tube 74. The swivel cup has an elliptical cross-section and fits over the distal end 42 of the balloon catheter having a similar elliptical cross-section to prevent rotation within the swivel cup and is positioned in the swivel mount 72 so that the central lumen and distal end of the catheter can rotate thereby transmitting torque through the stylet to furl the balloon by rotating handle 35. After furling the balloon, the stylet is removed from the central lumen 20 prior to insertion of the balloon catheter assembly into the patient. Although not generally required, a vacuum may be applied to the balloon to aid in maintaining it in a furled condition until it is inserted and positioned in the patient.

In an alternative embodiment, a stylet 70a is inserted into the central lumen 20 from the distal end 40. The stylet 70a (FIG. 7) is imbedded in a swivel cup 75a for free rotation therein. The swivel cup 75a has an elliptical cross-section as above and fits over the distal end 40 of the balloon catheter 10 which also has an elliptical cross-section that fits readily into the swivel cup. Again the swivel cup 75a is mounted in a swivel mount 72 so that the distal end of the catheter can rotate thereby transmitting torque through the stylet to furl the balloon. Stylet 70a has a flattened end 76 with a generally rectangular cross-section which protrudes from female luer type of fitting 60 at the end of wye 30 (FIG. 8). A male luer type of fitting 65 having a rectangular recess 77 for accepting end 76 of stylet 70a is used to rotate the stylet 70a with handle 35. Because the distal end of the stylet freely rotates in the swivel mount 72, the balloon is furled around the central lumen. As is readily apparent, other convenient cross-sectional shapes can be used for end 76 and recess 77 and for the swivel cup 75 or 75a and the distal end 42 of the catheter.

After the balloon catheter assembly in accord with the present invention is inserted and positioned in the patient, the balloon is unfurled by rotating handle 35 in the counter clockwise direction 80, i.e. the direction that transmits positive rotational torque throughout the length of central lumen 20. In this direction, the spiral-wrapped wire is rotated in a direction that tends to close the spirals on each other and, thus, provides positive torque transmission along the central lumen 20. When the rotation is limited by the washers 36 within handle 35, the fully unfurled position (i.e. position as originally assembled) is automatically assured.

The balloon catheter is then connected through conduit 31 to a console containing conventional pumping means for inflating and deflating the balloon.

The invention has been described in detail with reference to the preferred embodiments thereof. However, it will be appreciated that those skilled in the art, upon consideration of this specification and the embodiments described herein, may make variations, modifications and improvements within the spirit and scope of the invention, which is defined by the following claims.

We claim:

1. A balloon catheter comprising:
    a catheter having a proximate end and a distal end;
    an inflatable and deflatable balloon having a proximate end and a distal end, said proximate end of the balloon being sealably attached to the distal end of the catheter for admitting fluid and withdrawing fluid from the balloon; and
    a central lumen disposed within said catheter and said balloon and extending the length of said catheter, said central lumen having a proximate end and a distal end, said distal end of said central lumen being sealably attached to the distal end of the balloon;
    said central lumen comprising a flexible core wrapped spirally with a spring-like material so that the wrapped core can transmit positive torque when rotated in the direction that tends to close the spiral wrap, wherein said spring-like material is made of a flat wire stock having a rectangular cross-section.

2. The balloon catheter of claim 1 wherein said flexible core is a hollow tube.

3. The balloon catheter of claim 1 wherein said flexible core is made of an elastomeric or polymeric material.

4. The balloon catheter of claim 1 wherein said wire is made of surgical grade stainless steel.

5. The balloon catheter of claim 1 further comprising a stylet inserted in said central lumen from said proximate end, and a swivel cup fitted over the distal end of said balloon, said swivel cup and said distal end of said balloon having similar cross-sectional shapes that interlock to prevent rotation of the end within the swivel cup, said swivel cup having a swivel tube mounted for free rotation therein, said swivel tube having an end adapted to receive the end of said stylet.

6. The combination comnprising the balloon catheter of claim 1 and a swivel cup that fits over the distal end of said balloon, said swivel cup and said distal end of said balloon having similar cross-sectional shapes that interlock to prevent rotation of the end within the swivel cup, said swivel cup having mounted therein a stylet that extends to the proximate end of the central lumen, said balloon catheter further comprising an end piece having a male luer type of fitting and a recess with the same cross-sectional shape as the proximate end of the stylet wherein said end piece can receive said stylet and aid in rotating the stylet.

7. A method for cardiac assistance comprising:
preparing a balloon catheter in accord with claim 1 for insertion into a patient by furling the balloon around said central lumen by rotating said central lumen in the direction in which the spiral wrap tends to open;
inserting said balloon catheter into the patient and positioning the balloon in the desired location in the aorta;
unfurling the balloon by turning the central lumen so that the spiral wrap is rotated in the direction that tends to close the spiral, thereby transmitting positive rotational torque along said central lumen to unfurl said balloon; and
connecting said balloon catheter to a balloon pump for cardiac assistance.

8. The method of claim 7 wherein a stylet is used in the balloon catheter preparing step to aid in furling the balloon around the central lumen.

9. The method of claim 7, wherein said central lumen comprises a hollow core and said step of inserting said balloon catheter further comprises placing a guide wire inside said central lumen to aid in inserting and positioning the balloon in the aorta, after which the guide wire is removed.

10. The method of claim 7 wherein the step of preparing the balloon catheter further comprises drawing a vacuum on said balloon after it is furled around the central lumen, and said method further comprises the step of maintaining said vacuum until after the balloon is positioned in the aorta.

11. The method of claim 7 wherein a stylet is inserted into the central lumen to furl said balloon.

12. The method of claim 11 wherein said stylet is inserted from the distal end of the central lumen.

13. The method of claim 11 wherein said stylet is inserted from the proximate end of the central lumen.

* * * * *